US00PP15334P2

(12) United States Plant Patent
Fryer

(10) Patent No.: US PP15,334 P2
(45) Date of Patent: Nov. 16, 2004

(54) FLORIBUNDA ROSE PLANT NAMED 'FRYCENTURY'

(50) Latin Name: *Rosa hybrida*
Varietal Denomination: FRYcentury

(75) Inventor: Gareth Fryer, Knutsford Cheshire (GB)

(73) Assignee: Roses by Fred Edmunds, Inc., Wilsonville, OR (US)

( * ) Notice: Subject to any disclaimer, the term of this patent is extended or adjusted under 35 U.S.C. 154(b) by 0 days.

(21) Appl. No.: 10/693,273

(22) Filed: Oct. 24, 2003

(51) Int. Cl.[7] ..... A01H 5/00
(52) U.S. Cl. ..... Plt./143
(58) Field of Search ..... Plt./143

*Primary Examiner*—Anne Marie Grunberg
*Assistant Examiner*—Annette H Para
(74) *Attorney, Agent, or Firm*—Christie, Parker & Hale, LLP

(57) ABSTRACT

A new variety Floribunda rose, (*Rosa hybrida*) suitable for garden decoration, having flowers of pale peach and pink coloration.

1 Drawing Sheet

Classification: The present invention relates to a new *Rosa hybrida* plant.

Variety denomination: The new plant has the varietal denomination 'FRYcentury'.

BACKGROUND OF THE INVENTION

This invention relates to a new and distinct variety of Floribunda Rose. The varietal denomination of the new variety is 'FRYcentury'. It has as its seed parent the variety known as Silver Jubilee and as its pollen parent the unpatented variety known as an unpatented, unnamed seedling bred from 'FRYrelax' (Pensioner's Voice)×'Cheshire Life'.

SUMMARY OF THE INVENTION

Among the features that distinguish the new variety from other presently available and known commercial rose cultivars are the following combination of characteristics: its multi-colored blossoms with perfect spiral form and its healthy, shiny dark green foliage. The plant is a bushy, upright growing and slightly spreading plant, suitable for outdoor garden decoration.

Asexual reproduction of the new variety by budding as performed in Wilsonville, Oreg., and Kern County, Calif. shows that the foregoing and other distinguishing characteristics come true to form and are established and transmitted through succeeding propagations. 'FRYcentury' may be asexually propagated by cuttings, budding, grafting, layering or tissue culture.

COMPARISON WITH PARENTS

The new rose may be distinguished from its seed parent, 'Silver Jubilee' by the following combination of characteristics: 'Silver Jubilee' is a hybrid tea of small to medium size borne on short stems on a short densely foliage plant. The colors are a blend of medium and light pink with very little yellow. 'FRYcentury' is a blend of yellow and pink and comes on in clusters of flowers.

The new variety may be distinguished from its pollen parent, unnamed seedling bred from 'FRYrelax'×'Cheshire Life' by the following combination of characteristics: the unnamed seedling is a creamy pink hybrid tea with no yellow coloring.

The unnamed seedling's pollen parent, 'Cheshire Life', is an orange-vermilion hybrid tea. The unnamed seedling's seed parent, 'FRYrelax' is an orange-apricot floribunda.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon The Colour Chart of The Royal Horticultural Society of London, England, except where common terms of color definition are employed.

DESCRIPTION OF THE NEW VARIETY

The following description is of rose plants of the new cultivar grown outdoors in Wilsonville, Oreg. in the month of September. Phenotypic expression may vary with environmental, cultural and climatic conditions, as well as differences in conditions of light and soil.

'FRYcentury' is a new floribunda in the class *Rosa hybrida* with large flower size produced primarily in small (3–5 flowers) clusters. The color is light pink with pale apricot shadings in the center fading to pale pink with pale peach shading in the heart of the bloom at finish.

Flowers are high centered with an imbricate form and are carried upright. Bloom during the season is nearly continuous. The plant is upright with shiny, dark green foliage that is very resistant to disease.

FLOWER

The new variety bears its flowers usually in clusters of three to five or more per stem. Flowers are borne in irregular flat clusters on strong long stems (about 50 to about 70 cm.). Outdoors, the plant blooms very freely nearly continuously during the growing season. The flowers have a slight to moderate tea fragrance.

BUD

The peduncle is about 6 to about 8 cm. in length, of average caliper, and usually erect. It is almost moderately smooth, with many hairs and prickles. Peduncle color is between 144B and 144C.

Before the calyx breaks, the bud is about 1.5 to about 2 cm. in diameter at the widest point, about 2 to about 2.5 cm. in length, and pointed in shape with a conspicuous neck. The surface of the bud bears some foliaceous appendages moss tomentum and stipitate glands, usually with slender much cut bristle-like foliaceous parts extending beyond the tip of the bud about ½ or more of its length. Bud color is between 144B and 144C.

The inner surface of the sepals is covered and edged with fine wooly tomentum; sepal margins are lined with few stipitate glands.

As the petals open (after the calyx breaks), the bud is about 3 to about 3.5 cm. in diameter at the widest point, about 3.5 to about 4 cm. in length, and moderately pointed in form. The color of the under surface of the newly opened petals is between 12C and 12D. At the point where the petal attaches, there is a moderately large zone of near 12B. The 2 outer guard petals are often brushed 48A to 48B. The color of the upper surfaces of the newly opened petals is between 19A and 19B. At the point where the petal attaches, there is a moderately large zone of near 12B.

BLOOM

When fully open, the bloom ranges from about 8 to about 10 cm. in diameter. Petalage is double with about 24 to 30 petals and about 2 to 4 petaloids arranged irregularly. When partially open, the bloom form is moderately full to high centered and the petals are loosely spiraled with petal edges moderately reflexed outward. When fully open, the bloom form is moderately cupped, and the petals are loosely imbricated with petal edges moderately reflexed outward. Pistils and stamens are evident when fully open.

PETALS

The substance of the petals is moderately crisp and of medium thickness, with upper surfaces satiny and under surfaces moderately shiny. The outer petals are broadly round to ovate in shape with apices somewhat rounded to flat. The inner petals are broadly ovate in shape with apices moderately rounded. The petal width is from about 5.5 to about 6.5 cm and the petal length is from about 5.5 to about 7.0 cm. Outer rows of petals tend to be slightly longer and wider than the inner rows.

The petaloid surface is between 21A and 26B with a reverse color between 20A and 20B. The length of the petaloids are from about 1.5 cm to about 3.0 cm and their width is from about 0.5 cm to about 1.7 cm. The petaloids are highly convoluted with the upper surface satiny in texture and the lower surface shiny.

NEWLY OPENED FLOWER

The under surface of the outer petals is between 23D and 24D. At the point where the petal attaches, there is a somewhat large zone of between 12A and 12B. The upper surface of the outer petals is between 26C and 26D. At the point where the petal attaches, there is a moderately large zone of near 14B.

The under surface of the intermediate petals is between 27A and 27B. The upper surface of the intermediate petals is between 26C and 26D.

The under surface of the inner petals is between 26C and 26D. The upper surface of the inner petals is between 28C and 28D.

The general tonality of the newly opened flower is between 23B and 26B.

THREE-DAY-OLD-FLOWER

The under surface of the outer petals is near 20D. At the point where the petal attaches, there is a large zone of between 12B and 12C. The upper surface of the outer petals is between 49C and 49D. At the point where the petal attaches, there is a moderately large zone of between 12B and 12C.

The under surface of the inner petals is between 20C and 20D. The upper surface of the inner petals is between 20C and 22D.

The general tonality of the three-day-old-flower is between 22C and 23D.

On the spent bloom, the petals usually drop off cleanly and are not particularly affected by cold, hot, wet, or dry weather except fading accelerates in hot weather.

In September in Wilsonville, Oreg., blooms on the bush growing outdoors generally last about four to five or more days. Cut roses from plants grown outdoors and kept at normal indoor living temperatures generally last about three to four or more days.

MALE REPRODUCTIVE ORGANS

Stamens are average in number (approximately 125) and are arranged irregularly about the pistils. The filaments are short without anthers. Filaments are between 14B and 14C in color. The anthers are somewhat small for the class and all open approximately at the same time. Anther color is near 11A when immature and between 14A and 15A at maturity. Pollen is sparse to moderate and near 23A in color.

FEMALE REPRODUCTIVE ORGANS

Pistils are few in number (approximately 30). Between the stamens and the pistils there appears a large number of foliaceous pistils without stigmatic surface. The styles are very uneven, moderately short in length, moderately heavy in caliper, and densely bunched. Stigma color is between 2A and 3A. Style color is between 1A and 1B and very tomentose. Ovaries are usually all enclosed in the calyx.

Hips have not been observed on this variety when grown in Wilsonville, Oreg. Generally hips turn brown and absciss without setting seed.

FOLIAGE

The compound leaves are usually comprised of three to five leaflets and are borne abundantly. The leaves are about 4 to about 6.5 cm. in length and about 3 to about 4.5 cm. in width at the widest point, moderately leathery to crisp in texture, and semi-glossy in finish. The terminal leaflets are about 6 cm. in length and about 4 cm. in width at the widest point, shaped somewhat oval to ovate with moderately acuminate apices and round bases. Their margins are usually simply serrate.

The upper surface of the mature leaf is between 137A and 137B. The under surface of the mature leaf is between 138B and 138C. The upper surface of the young leaf is between 152B and 152C, sometimes heavily suffused with near 60B especially along the margins of the terminal leaves. The young leaves are very shiny. The under surface of the young leaf is near 144C, lightly suffused with near 60B.

The rachis is light in caliper and somewhat smooth. The upper side is shallowly grooved with few hairs and stipitate glands on the edges of the grooves. The under side of the rachis is very smooth with few prickles.

The stipules are about 1 to about 1.5 cm. in length and moderately narrow width with long straight points that usually turn out at an angle of less than 45 degrees.

The plant displays an above average degree of resistance to powdery mildew and blackspot and rust as compared to other commercial varieties grown under comparable conditions in Wilsonville, Oreg.

GROWTH

The plant has a bushy, upright, slightly spreading, medium height growth habit (about 125 to about 150 cm. in height and about 65 to about 80 cm. spread at the widest point), with moderately full branching. It displays moderately vigorous growth and the canes are of moderately light to medium caliper for the class.

The color of the major stems is between 143B and 143C. They bear few large prickles that are about 1 to about 1.5 cm. in length. The large prickles are almost straight with a moderately medium length to broad rounded base; prickle color is between 173A and 175A. The major stem bears very few small prickles of similar shape and coloration and which are between 173A and 175A in color. There are no coarse hairs.

The color of the branches is between 143B and 143C. They bear few large prickles which are of similar size and shape to the large prickles on the major stems; prickle color is between 164D and 165D and slightly translucent. The branches bear few small prickles of similar shape and coloration and which are between 164D and 165D in color. There are no coarse hairs.

The color of the new shoots is between 144B and 145A sometimes lightly suffused with near 60B. They bear few large prickles, which are of similar size and shape to the large prickles on the major stems; prickle color is between 164D and 165D. The shoots bear few small prickles of similar shape and coloration. There are no coarse hairs.

I claim:

1. A new and distinct Floribunda rose plant of the variety 'FRYcentury' substantially as described and illustrated herein.

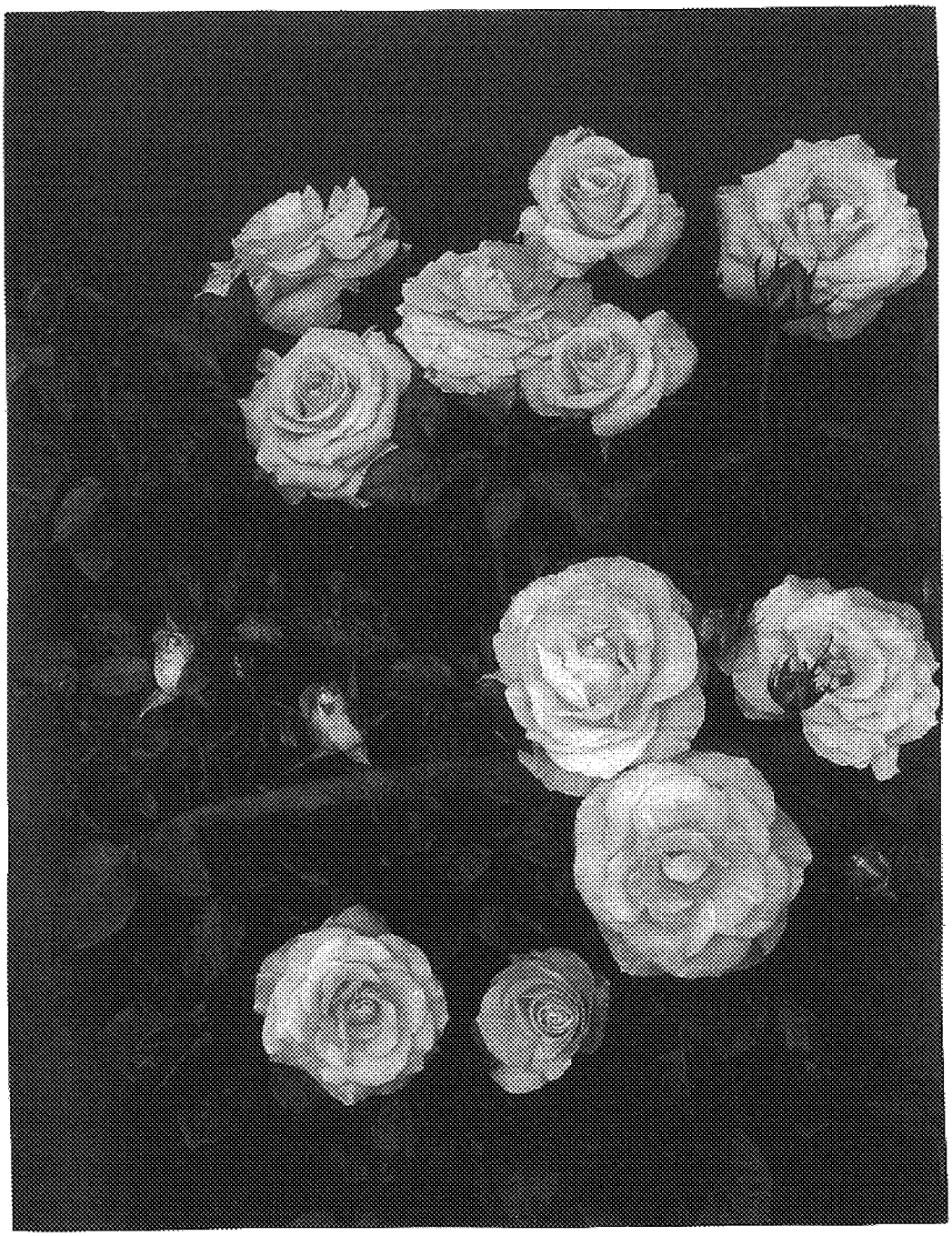

* * * * *